United States Patent
Huckman et al.

(10) Patent No.: US 6,677,480 B2
(45) Date of Patent: Jan. 13, 2004

(54) PROCESS CONTROL IN PRODUCTION OF ACETIC ACID VIA USE OF HEAVY PHASE DENSITY MEASUREMENT

(75) Inventors: Michael E. Huckman, Corpus Christi, TX (US); G. Paull Torrence, Corpus Christi, TX (US); Hung-Cheun Cheung, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 132 days.

(21) Appl. No.: 10/058,547

(22) Filed: Jan. 28, 2002

(65) Prior Publication Data

US 2003/0144548 A1 Jul. 31, 2003

(51) Int. Cl.[7] ............................................. C07C 51/12
(52) U.S. Cl. ........................................ 562/519; 562/517
(58) Field of Search ................................... 562/519, 517

(56) References Cited

U.S. PATENT DOCUMENTS

| | | | |
|---|---|---|---|
| 3,769,329 A | 10/1973 | Paulik et al. ............ 260/488 K |
| 5,001,259 A | 3/1991 | Smith et al. ................ 562/519 |
| 5,026,908 A | 6/1991 | Smith et al. ................ 562/519 |
| 5,144,068 A | 9/1992 | Smith et al. ................ 562/519 |
| 5,474,774 A | 12/1995 | Walker et al. .............. 424/195 |
| 6,103,934 A | * 8/2000 | Hallinan et al. ............ 562/517 |
| 6,255,527 B1 | * 7/2001 | Muskett ...................... 562/519 |

FOREIGN PATENT DOCUMENTS

| | | | | |
|---|---|---|---|---|
| EP | 1 002 785 A1 | 3/2000 | ............ B01J/19/00 |
| EP | 1002785 A1 | * 5/2000 | |

OTHER PUBLICATIONS

Roth, James F., et al, Chem Tech, Oct. 1971, pp 600–604.

* cited by examiner

*Primary Examiner*—Paul J. Killos
*Assistant Examiner*—Hector M Reyes
(74) *Attorney, Agent, or Firm*—M. Susan Spiering

(57) ABSTRACT

A process for monitoring and controlling reactor conditions during the production of acetic acid by the catalyzed carbonylation of methanol is provided. The process of the present invention comprises measuring the density of the heavy phase of the light ends distillation column in the purification system of the carbonylation process. The density measurement is used to adjust the feed of methanol and/or to regulate the temperature in the reaction zone to optimize reactor conditions. The density measurement may also be used to adjust other parameters in the reactor system. The invention is also directed to the system for manufacturing acetic acid based on the process control procedure described.

27 Claims, 2 Drawing Sheets

PROCESS CONTROL IN PRODUCTION OF ACETIC ACID VIA USE OF HEAVY PHASE DENSITY MEASUREMENT

BACKGROUND OF THE INVENTION

1. Field of the Invention

This invention relates to a method of improving process control in the manufacture of acetic acid, and a method of manufacturing acetic acid utilizing improved process control.

2. The Related Art

Among currently employed processes for synthesizing acetic acid, one of the most useful commercially is the catalyzed carbonylation of methanol with carbon monoxide as disclosed in U.S. Pat. No. 3,769,329. This patent discloses the use of a rhodium based carbonylation catalyst, either dissolved or otherwise dispersed in a liquid reaction medium or else supported on an inert solid, along with a halogen-containing catalyst promoter as exemplified by methyl iodide. However, it is understood that various catalyst systems, particularly those incorporating Group VIII metals, may be used for the production of acetic acid through the carbonylation of methanol. Generally, the carbonylation reaction is conducted with the catalyst being dissolved in a liquid reaction medium through which carbon monoxide gas is continuously bubbled. U.S. Pat. No. 3,769,329 discloses that water may be added to the reaction mixture to exert a beneficial effect upon the reaction rate, and water concentrations between about 14–15 wt. % are typically used. This is the so-called "high water" carbonylation process.

An alternative to the "high water" carbonylation process is the "low water" carbonylation process, as described in U.S. Pat. Nos. 5,001,259, 5,026,908, and 5,144,068. Water concentrations below 14 wt. % and even below 10 wt. % can be used in the "low water" carbonylation process. Employing a low water concentration simplifies downstream processing of the desired carboxylic acid to its glacial form.

U.S. Pat. No. 5,144,068 discloses that, at low water concentrations, there is a synergistic effect between the methyl acetate concentration in the carbonylation reactor and the concentration of iodide salt used to stabilize the rhodium catalyst. It also teaches that an unexpected advantage of operating the reactor at high methyl acetate is a reduction in the formation of undesirable reaction products. In particular, propionic acid is reduced by an order of magnitude. Carbon dioxide and hydrogen, which are formed by the water gas shift reaction, are also reduced.

Various means have been proposed for controlling the processes for the production of acetic acid. For example, U.S. Pat. No. 5,474,774 discloses a system for controlling the liquid levels in a reactor-flasher combination used for the carbonylation of methanol to acetic acid. Liquid level control is achieved by proportional controllers or other controllers, which proportionally change the liquid flow rates from the respective reactor and flasher. An adjustment can be made to the level controllers to change the liquid flow rates by a function generator, which adjusts the flow rate, according to an empirically derived function, which correlates changes in methanol feed rate to liquid flow rates from the reactor and flasher.

European Patent Application EP 1 002 785 A1 describes a process for the production of acetic acid in which the methyl acetate concentration in the liquid reaction composition is maintained at a pre-determined value by monitoring the ratio of methanol and/or reactive derivatives thereof to carbon monoxide being converted to acetic acid and adjusting the methanol, and/or reactive derivatives thereof, feed rate in response.

U.S. Pat. No. 6,103,934 discloses an acetic acid production process with a control process which measures various reactor component concentrations, specifically the active catalyst species, methyl iodide, water, and methyl acetate with an infrared analyzer, and adjusting in response thereto, the concentrations of the catalyst species, methyl iodide, and water to control the acetic acid reaction.

U.S. Pat. No. 6,255,527 B1 discloses an acetic acid production system with a method for controlling the carbon monoxide flow to a reactor by measuring carbon monoxide flowing through a control valve; performing a background calculation to arrive at a time-averaged carbon monoxide flow rate; determining a maximum carbon dioxide flow rate; and controlling the carbon monoxide flow rate so that it does not exceed the calculated maximum flow rate.

All patents and publications referred to herein are hereby incorporated by reference in their entireties.

SUMMARY OF THE INVENTION

The present invention relates to a process for monitoring and controlling reactor conditions during the production of acetic acid by the catalyzed carbonylation of methanol. The process of the present invention comprises measuring the density of the heavy phase of the light ends distillation column in the purification system of the carbonylation process. The density measurement is used to adjust the feed of methanol and/or to regulate the temperature in the reaction zone to optimize reactor conditions. The density measurement may also be used to adjust other parameters in the reactor system. The invention is also directed to the system for manufacturing acetic acid based on the process control procedure described.

Monitoring the heavy phase density in accordance with the present invention may be performed near in time to removal of a sample or alternatively, the monitoring may be conducted online. Online monitoring refers to the analysis of heavy phase in real time or substantially real time either by direct insertion of a densitometer probe into the heavy phase process vessel or by rapidly circulating heavy phase process solution through a densitometer and subsequently returning this solution to the process. Off-line measurement refers to the irreversible removal of a heavy phase sample from the process and subsequent analysis being performed on laboratory instrumentation. Further, adjustment of component concentrations and reaction parameters as required should occur substantially immediately following characterization of the sample. This adjustment may be performed automatically in response to the heavy phase density measurement. Finally, it is preferred that the sampling be performed often to minimize undesirable drift from optimum reaction efficiency.

These and other objects and advantages of the present invention shall become more apparent from the accompanying drawings and description thereof.

DETAILED DESCRIPTION OF THE INVENTION

The present invention relates to a continuous carbonylation process for the production of acetic acid and in particular to a process for the production of acetic acid by the carbonylation of methanol and/or a reactive derivative thereof in the presence of a catalyst system which may comprise, for example, a Group VIII metallic element, particularly Rh, Ir, Co, Ni, Ru, Pd or Pt, and most often Rh or Ir, a halogen promoter, most often a hydrogen halide or organic halide, particularly an alkyl iodide such as methyl iodide, a stabilizer/copromoter, which is a salt of a metal of Group IA or IIA of the Periodic Table, or a quatenary ammonium or phosphosium salt, particularly an iodide or acetate salt and most often lithium iodide, or lithium acetate.

Figure 1:
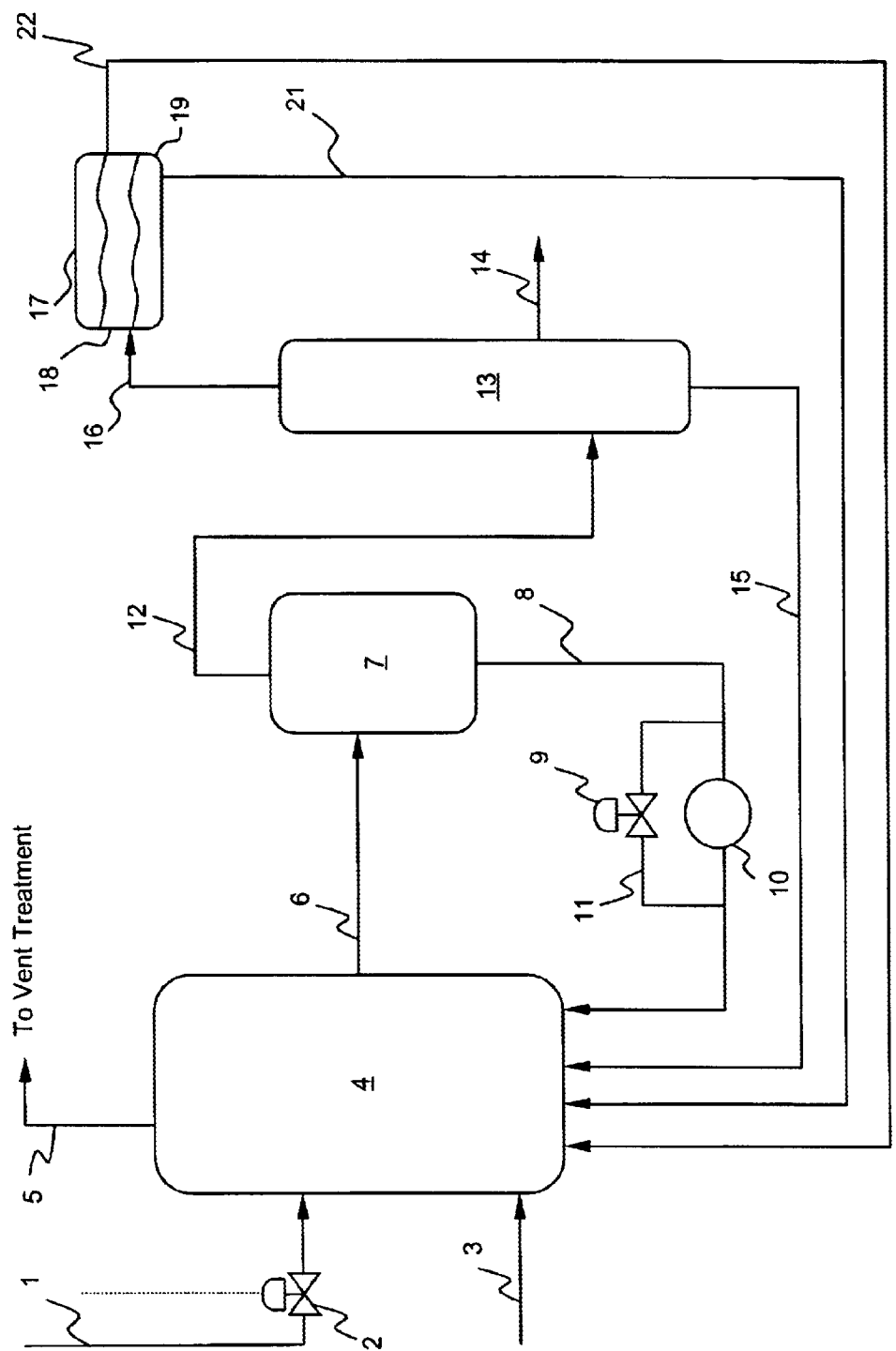
FIG. 1 is a schematic diagram of a typical continuous process for the production of acetic acid.

The continuous carbonylation process may be thought of as comprising three basic sections: the reaction, purification, and off-gas treatment sections. This process is represented schematically in FIG. 1. The reactor 4, which may be a stirred tank reactor, is operated at adjustable elevated temperatures and pressures. As the reaction proceeds in the reactor 4, the liquid reaction mixture is withdrawn from the reactor and passed to a flash tank 7 where the majority of the lighter components of the liquid reaction mixture (methyl iodide, methyl acetate, unreacted methanol, and water) together with product acetic acid are vaporized. The vapor fraction is then directed to the purification section and the liquid fraction (comprising the noble catalyst dissolved in acetic acid) and any remaining light components is recycled to the reactor 4. The purification section typically comprises a first distillation column 13 (the light ends column), a second distillation column (the drying column, not shown) and a third distillation column (the heavy ends column, not shown). In the light ends column 13, methyl iodide, methyl acetate, and unreacted methanol are removed overhead along with some water and acetic acid in stream 16. The vapor is condensed and allowed to separate into two phases in a decanter 17, both phases are usually returned to the reactor. One phase of this condensate, the upper layer, is the lighter phase 18 comprised primarily of water and acetic acid in which lesser amounts of methyl acetate and methyl iodide may be present. The light phase may be returned to the reactor in the light phase recycle line 22. The other phase, the lower layer, is the heavy phase 19 comprised primarily of methyl iodide and methyl acetate in which lesser amounts of water, methanol, and acetic acid may be present. The heavy phase may be returned to the reactor in the heavy phase recycle line 21. It is the density of this heavy phase which provides feedback data for controlling the reactor composition in accordance with the present invention. In particular, the present invention involves monitoring the density of this heavy phase during continuous reactor operation as an indicator of the level of methyl acetate in the reaction zone. Based upon this density measurement, the continuous carbonylation process can be altered to prevent undesirable process excursions during the production of acetic acid.

Wet acetic acid is removed as a side stream 14 from the light ends column and is fed to a drying column (not shown) where water is removed overhead and an essentially dry acetic acid stream is removed from the base of the distillation zone. The overhead water stream from the drying column is recycled to the reaction section. Heavy liquid by-products are removed from the base of a heavy ends column with product acetic acid being removed as a side stream.

In some chemical processes, it is necessary to monitor the progress of the chemical reaction and to adjust the supply of the reactants to ensure that the reaction proceeds as desired. The production of acetic acid is one such chemical process. One method of manufacturing acetic acid, by carbonylation of methanol or its derivatives, such as methyl acetate or methyl iodide, involves a chemical reaction initiated by a catalyst system as described previously. Carbonylation has become a preferred route to make acetic acid. Nevertheless, there are countervailing considerations which affect implementation of this process. First, the underlying reaction chemistry is intricate, involving a number of interrelated reactions, by-products and equilibriums, all of which must be properly balanced, one against the other, to make the process practicable and maximize efficiency of raw material utilization. Also, the catalyst systems, such as coordination compounds of rhodium, iridium and the like, required for carbonylation are generally complex and expensive. Moreover, carbonylation catalyst systems are extraordinarily sensitive to changes in any number of reaction parameters which, in turn, adversely affect catalyst stability and activity.

Manually sampling the reactor effluent and performing a separate laboratory analysis of component concentrations using various laboratory techniques is sometimes utilized. This procedure is labor intensive and time consuming, resulting in long time lapses between sampling and the characterization of the sample. This method of sample characterization significantly limits the number of data points per day for a given reactor, to usually about 6 to about 12. Additionally, and more importantly, because of the delay between sampling and generation of data, the sample characterization provides an evaluation of the reactor system that lags behind the actual status of the system by several hours. Various means have been proposed for remedying such problems. For example, Fourier Transform Infrared Spectrometers are used to continuously monitor the components of a reaction process. This type of monitoring system is disclosed in U.S. Pat. No. 6,103,394. Additionally, monitoring systems based upon gas chromatography technology have been used. However, both of these types of systems have significant disadvantages in terms of the high level of maintenance and expense necessary to maintain the equipment in an accurate functioning state. Additionally, the gas chromatography systems may require a considerable period of time to analyze a sample, resulting in a lag between the results and the actual status of the process system as mentioned above.

It is therefore desirable to provide a monitoring system that facilitates more frequent monitoring of the chemical reaction in the production of acetic acid so that changes in the reaction zone can be detected early and to generate appropriate feedback to change the reaction conditions. The present invention provides this early detection capability by relying upon analytical samples taken from outside of the reaction zone. In accordance with the present invention, the heavy phase density is measured. The heavy phase density is a function of the concentration of methyl iodide and methyl acetate in the heavy phase. In turn, the concentration of methyl iodide and methyl acetate in the heavy phase is indicative of the concentration of methyl acetate in the reaction zone. In particular, as the methyl acetate level increases in the reaction zone, the density of the heavy phase decreases because more methyl acetate is sent forward to the light ends distillation column and then concentrates, predominately in the heavy phase. Because methyl acetate is less dense than methyl iodide, the density of the heavy phase decreases as the methyl acetate concentration increases. Making use of this relationship, the present invention provides a convenient, safe, and relatively inexpensive method to continuously monitor the level of methyl acetate in the reaction zone.

The present invention relates to control of a continuous carbonylation process based upon feedback derived from measuring the density of the heavy phase of the light ends distillation column in the purification section of the carbonylation process. During continuous operation it is customary to feed carbon monoxide on demand under pressure control, and methanol to a reactor with a liquid composition comprising standard concentrations of methyl acetate, water, a catalyst system as described previously, with the remainder of the composition being acetic acid. In the reactor, carbonylation occurs to produce acetic acid which is removed with the reaction liquid. Thereafter acetic acid is recovered as described above. Unconverted carbon monoxide is vented from the reactor and after recovery of volatile components there from is generally discarded. At methyl acetate concentrations in the reactor liquid of about 3 wt. % or less, which levels are generally associated with the use of rhodium catalysts, the reaction rate depends strongly on methyl acetate concentration. Under these circumstances little, if any, difficulty is typically experienced in controlling reaction section methyl acetate concentrations using reaction temperature. However, as methyl acetate concentrations approach 5 wt. % or greater, the reaction rate is significantly less dependent on methyl acetate concentration. In this situation, there is an increased potential for the reactor methyl acetate concentration to increase rapidly. This increase will cause significant disturbances in downstream equipment and the plant may trip which is undesirable because it interrupts production and creates a potentially dangerous situation. Unsteady reactor methyl acetate concentration also leads to instability in reactor carbon monoxide uptake. This may lead to the necessity to vent carbon monoxide for control purposes, resulting in a loss of carbon monoxide conversion efficiency. Control of reactor methyl acetate concentrations at high methyl acetate concentrations is therefore a significant problem.

Although it may be more difficult to control reactor conditions at higher concentrations of methyl acetate, it is nonetheless desirable to operate at high methyl acetate concentrations because certain beneficial effects are seen at higher concentration levels. Notable beneficial effects are the ability to operate with lower catalyst concentrations, reduced propionic acid production, and a reduction in the water gas shift reaction resulting in improved CO efficiency. Under certain circumstances, it may be desirable to operate at methyl acetate concentrations up to 10 wt. % or even higher. The present invention allows for stable operation of the reaction system at such high methyl acetate concentrations.

The present invention provides a means for preventing such process excursions during continuous processes for the production of acetic acid by providing a means to continuously monitor reactor methyl acetate concentration and to control the reaction process in response thereto in order to stabilize the methyl acetate concentration.

It has been found that a methyl acetate concentration of about 2 wt. % in the reaction zone generally corresponds to a heavy phase density in the range of about 1.90 to about 2.0. At 4.5 wt. % methyl acetate concentration in the reaction zone, the density of the heavy phase will typically be in the range from about 1.70 to about 1.80. As mentioned above, as methyl acetate concentrations in the reaction zone during the production of acetic acid approach 5 wt. %, the likelihood of a reactor excursion is increased. At methyl acetate concentrations of about 6 wt. %, the density of the heavy phase will typically be in the range from about 1.5 to about 1.6. However, it is understood that these are only general parameters. The exact density for a given mode of operation depends on the concentration of other species in the reactor liquid such as water and methyl iodide, as well as the manner of operation of the light ends column.

Table 1 sets forth a series of data depicting various methyl acetate concentrations over a range from about 2.0 wt. % to about 7.0 wt. % with corresponding heavy phase density values measured in a typical acetic acid production system.

TABLE I

Heavy Phase Density Values

| Reactor<br>Methyl Acetate Conc. | Heavy Phase<br>Density |
|---|---|
| 1.7 | 1.97 |
| 2.0 | 1.95 |
| 2.3 | 1.93 |
| 2.8 | 1.89 |
| 3.0 | 1.87 |
| 3.4 | 1.84 |
| 3.8 | 1.79 |
| 4.1 | 1.78 |
| 4.4 | 1.77 |
| 4.5 | 1.75 |
| 4.7 | 1.71 |
| 5.0 | 1.70 |
| 5.5 | 1.61 |
| 5.7 | 1.59 |
| 6.0 | 1.58 |
| 6.2 | 1.51 |
| 7.0 | 1.48 |
| 7.1 | 1.45 |

Generally, this data demonstrates that the density of the heavy phase will increase or decrease in the range from about 0.05 to about 0.1 with each 1 wt. % decrease or increase in methyl acetate wt. % concentration in the reaction zone. However, the specific corresponding density range will vary from reaction system to reaction system. Accordingly, it will generally be necessary to calibrate the relationship between methyl acetate concentration and the heavy phase density for each reaction system in which the present invention is practiced.

Once the relationship between reactor methyl acetate concentration and the heavy phase density for a given reaction system is known, the present invention provides a means for accurately and continuously monitoring the reaction zone methyl acetate concentration and providing feedback to change or maintain reaction parameters in response to this feedback.

The reaction parameters may be changed in a variety of ways. One such way is to change the methanol feed rate to the reactor. Another way is to change the reaction temperature. This is often accomplished by adjusting the temperature of a recycle stream flowing back to the reactor through one or more heat exchangers. Additionally, the temperature of the reaction system may be regulated, in whole or in part, by adjusting the temperature of other streams entering the reaction system, such as a pump-around stream. Other parameters which may be adjusted in accordance with the present invention include water concentration in the reactor, catalyst concentration, methyl iodide concentration, and CO partial pressure in the reaction system. By changing any of these variables, or a combination of more than one of the variables, it is possible to exert at least some control on the reactor methyl acetate concentration.

In accordance with one embodiment of the present invention, if the heavy phase density decreases to a level indicating that the methyl acetate concentration is rising into a zone prone to a loss of control of the reaction system, the process of the present invention is programmed to respond (or an operator will manually respond) by decreasing the methanol feed rate to the reactor, which will lower the rate of formation of methyl acetate in the reactor. In another embodiment, the system of the present invention may be programmed to respond (or an operator will manually respond) by raising the temperature in the reactor to increase the rate at which methyl acetate is converted to acetic acid. In another embodiment, the system of the present invention is programmed to respond (or an operator will manually respond) by a combination of decreasing the methanol feed rate and raising the temperature in the reactor.

Conversely, if the feedback mechanism in accordance with the present invention indicates that the methyl acetate concentration in the reactor is falling below desired levels, the information may be used to increase methyl acetate levels rather than lowering them. In one embodiment of the present invention, if the heavy phase density increases to a level indicating that the methyl acetate concentration is falling below the desired level in the reactor, the process of the present invention is programmed to respond (or an operator will manually respond) by increasing the methanol feed rate to the reactor, which will increase the rate of formation of methyl acetate in the reactor. In another embodiment, the system of the present invention may be programmed to respond (or an operator will manually respond) by lowering the temperature in the reaction zone to decrease the rate at which methyl acetate is converted to acetic acid. In another embodiment, the system of the present invention is programmed to respond (or an operator will manually respond) by a combination of increasing the methanol feed rate and lowering the temperature in the reaction zone.

Figure 2:
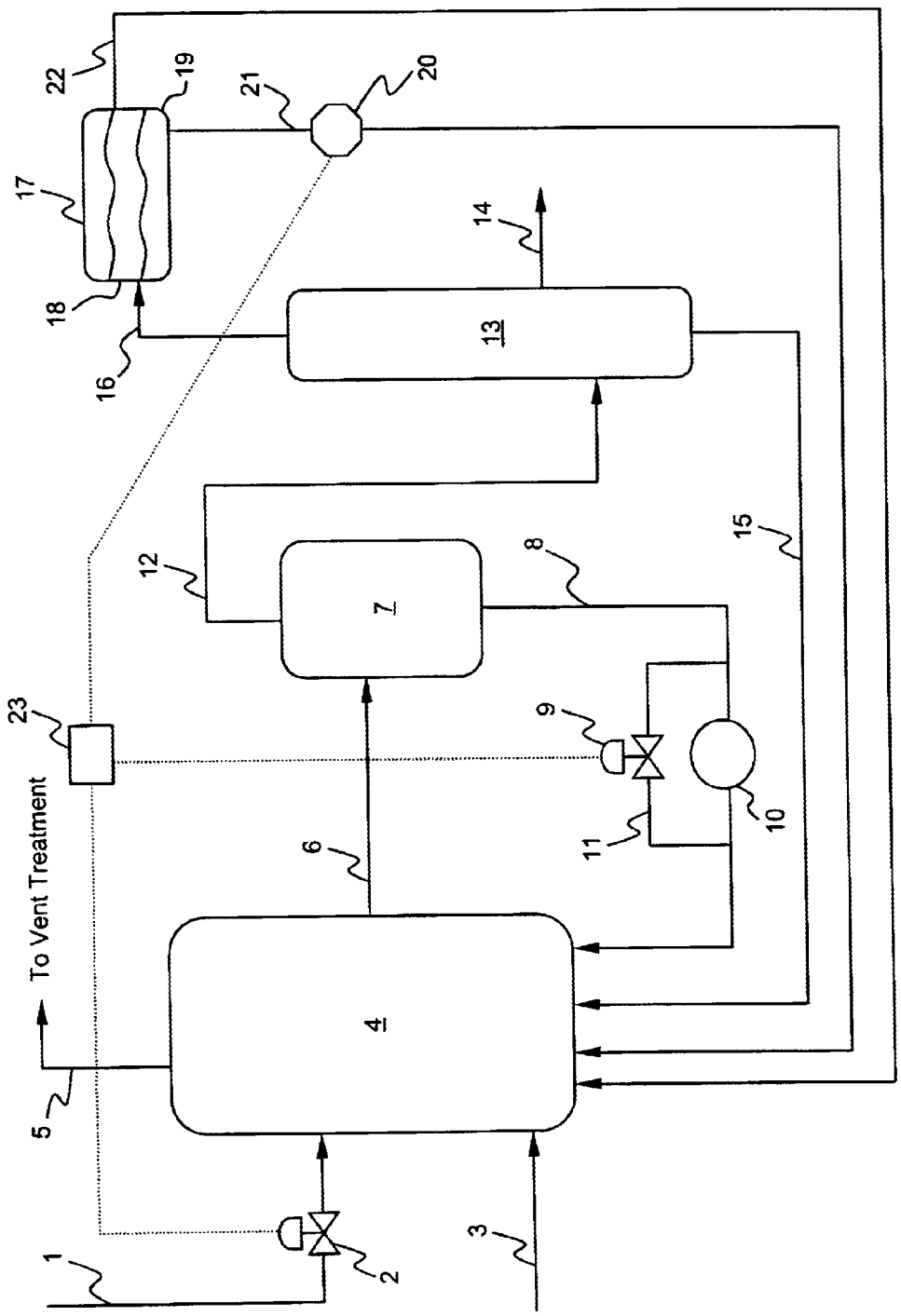
FIG. 2 is a diagram of the equipment arrangement used in accordance with an embodiment of the present invention.

FIG. 2 depicts an embodiment of the present invention demonstrating the placement of the components of the monitoring and feedback system. Any suitable density measuring device, such as a nuclear or optical densitometer 20 is provided in the heavy phase heavy phase recycle line 21. The densitometer 20 may be any of various commercially available densitometers such as the commercial nuclear densitometers manufactured by Berthold. A suitable model is the Berthold LB 386-1C. The densitometer allows for the continuous monitoring of the heavy phase liquid density. Alternatively, samples of the heavy phase may be taken and their densities determined off-line by any suitable density measuring device, such as an optical densitometer. Using this density, as described above, the methyl acetate concentration in the reaction zone can be determined quickly and accurately.

The system may be designed to allow the density measurement to be monitored by a system operator. Based upon desired methyl acetate concentrations in the reaction zone, the operator may use the measured density to determine when various changes are necessary in the process to maintain the methyl acetate concentration at the desired level. For example, in response to a heavy phase density measurement corresponding to a methyl acetate concentration higher than desired, the operator may choose to raise the temperature in the reactor by decreasing the flow rate to heat exchanger 10, which will have the corresponding effect of lowering the methyl acetate concentration. Alternatively, the operator may choose to decrease the methanol feed rate by increasing the flow through the methanol feed control valve 2. Additionally, the operator may choose to adjust the methyl acetate concentration to a desired operating level by employing a combination of corrections involving temperature and feed rate control. In a situation in which the densitometer indicates a methyl acetate concentration is lower than desired, the operator may seek corrective action in the opposite direction by increasing the flow rate through the heat exchanger 10 or increasing the flow rate through the methanol feed control valve or a combination of the two to raise the methyl acetate concentration.

In another embodiment of the present invention, the system is equipped with an automatic feedback control process. In this embodiment, the densitometer 20 may be wired, or otherwise in communication with, a control loop with a feedback control means 23 providing feedback to the control valve of the heat exchanger 10 and/or the control valve 2 for the methanol feed. In this embodiment the system maybe programmed to automatically control operation of the heat exchanger or the methanol feed or a combination of the two in response to deviations of the methyl acetate concentration from desired levels as indicated by the heavy phase density.

The foregoing disclosure and description of the invention are illustrative and explanatory thereof, and variations of the invention will be apparent to those skilled in the art, and are considered to be within the spirit and scope of the claimed invention.

We claim:

1. A method for effecting process control in a reaction for the production of acetic acid through the reaction of methanol and carbon monoxide in a reaction mixture comprising methyl acetate, comprising the steps of:

measuring the density of the heavy phase of a light ends distillation column comprising methyl iodide and methyl acetate; and controlling reaction conditions in the reactor in response to the measured density.

2. The method of claim 1 wherein the conditions of the reaction mixture are controlled by adjusting the temperature of the reaction mixture.

3. The method of claim 1 wherein the conditions of the reaction mixture are controlled by adjusting the flow of methanol to the reaction mixture.

4. The method of claim 1 wherein the conditions of the reaction mixture are controlled by adjusting the temperature of the reaction mixture and by adjusting the flow of methanol to the reaction mixture.

5. The method of claim 1 wherein the concentration of methyl acetate in the reaction mixture is from about 2.0 to about 10.0 wt. %.

6. The method of claim 5 wherein the concentration of the methyl acetate in the reaction mixture is greater than about 5 wt. %.

7. The method of claim 6 wherein the concentration of the methyl acetate in the reaction mixture is form about 4.0 to about 7 wt. %.

8. The method of claim 7 wherein the density of the heavy phase is from about 1.5 to about 1.8.

9. The method of claim 5 wherein an electronic signal indicative of the measured density of the heavy phase is sent to a control system which operates in a manner to control the reaction conditions in the reactor in response to the density of the heavy phase.

10. A method for manufacturing acetic acid through the reaction of methanol and carbon monoxide in a reaction mixture comprising methyl acetate with improved process control, comprising the steps of:

measuring the density of the heavy phase of a light ends distillation column comprising methyl iodide and methyl acetate; and controlling the conditions in the reaction mixture in response to the measured density.

11. The method of claim 10 wherein the conditions of the reaction mixture are controlled by adjusting the temperature of the reaction mixture.

12. The method of claim 10 wherein the conditions of the reaction mixture are controlled by adjusting the flow of methanol to the reaction mixture.

13. The method of claim 10 wherein the conditions of the reaction mixture are controlled by adjusting the temperature of the reaction mixture and by adjusting the flow of methanol to the reaction mixture.

14. The method of claim 10 wherein the concentration of methyl acetate in the reaction mixture is from about 2.0 to about 10.0 wt. %.

15. The method of claim 14 wherein the concentration of the methyl acetate in the reaction mixture is greater than about 5 wt. %.

16. The method of claim 15 wherein the concentration of the methyl acetate in the reaction mixture ranges form about 4.0 to about 7 wt. %.

17. The method of claim 16 wherein the density of the heavy phase is from about 1.5 to about 1.8.

18. The method of claim 14 wherein an electronic signal indicative of the measured density of the heavy phase is transmitted to a control system which operates in a manner to control the reaction conditions in the reactor in response to the density of the heavy phase.

19. A reaction system for the carbonylation of methanol to acetic acid comprising:
(a) reactor containing a liquid reaction medium comprising methanol, a catalyst, a solvent, and water to form a reactor product comprising acetic acid, methyl acetate, and methyl iodide;
(b) a flasher for receiving the reactor product form the reactor and capable of flashing off a portion of the reactor product to form an overhead stream comprising acetic acid, methyl acetate, and methyl iodide;
(c) means for directing the reactor product to the flasher;
(d) a light ends distillation column for receiving the overhead stream and capable of distilling the overhead stream to form a light phase and a heavy phase;
(e) means for directing at least a portion of the overhead stream to the light ends distillation column; and
(f) means for measuring the density of the heavy phase.

20. The reaction system according to claim 19 comprising means for controlling reaction conditions in the reactor in response to the density of the heavy phase.

21. The reaction system of claim 20 comprising means for generating an electronic signal indicative of the measured density of the heavy phase and transmitting the signal to a control system which operates in a manner to control the reaction conditions in the reactor in response to the density of the heavy phase.

22. The reaction system of claim 21 wherein the conditions of the reaction mixture are controlled by adjusting the flow of methanol to the reaction mixture.

23. The reaction system of claim 21 wherein the conditions of the reaction mixture are controlled by adjusting the temperature of the reaction mixture and by adjusting the flow of methanol to the reaction mixture.

24. The reaction system of claim 21 wherein the concentration of methyl acetate in the reaction mixture is from about 2.0 to about 10.0 wt. %.

25. The reaction system of claim 24 wherein the concentration of the methyl acetate in the reaction mixture is greater than about 5 wt. %.

26. The reaction system of claim 25 wherein the concentration of the methyl acetate in the reaction mixture is form about 4.0 to about 7 wt. %.

27. The reaction system of claim 26 wherein the density of the heavy phase is from about 1.5 to about 1.8.

* * * * *